US00PP32813P3

(12) United States Plant Patent
Iezzoni

(10) Patent No.: US PP32,813 P3
(45) Date of Patent: Feb. 16, 2021

(54) CHERRY TREE (ROOTSTOCK) NAMED 'LAKE'

(50) Latin Name: ***Prunus avium* L. and *Prunus fruticosa* Pall.**
Varietal Denomination: Lake

(71) Applicant: Board of Trustees of Michigan State University, East Lansing, MI (US)

(72) Inventor: Amy Iezzoni, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 419 days.

(21) Appl. No.: 15/330,734

(22) Filed: Oct. 31, 2016

(65) Prior Publication Data

US 2018/0124971 P1 May 3, 2018

(51) Int. Cl.

| | |
|---|---|
| ***A01H 5/06*** | (2018.01) |
| ***A01H 6/74*** | (2018.01) |
| ***A01H 5/08*** | (2018.01) |
| ***A01H 5/02*** | (2018.01) |

(52) U.S. Cl.
USPC ..... Plt./183
CPC ..... *A01H 5/08* (2013.01); *A01H 5/02* (2013.01); *A01H 6/7445* (2018.05)

(58) Field of Classification Search
USPC ..... Plt./156, 180, 181, 183
See application file for complete search history.

(56) References Cited

PUBLICATIONS

Warner, G. "New MSU cherry rootstocks are dwarfing and precocious: more trials for cherry rootstocks." Feb. 1, 2014. The Good Fruit Grower website http://www.goodfruit.com/more-trials-for-cherry-rootstocks/. 4 pages.*

Andersen, Kristen, et al. "Development of the Simple Sequence Repeat Marker PruG4RSfor the Differentiation of Cherry Rootstocks", Michigan State University, Poster, (2015).

* cited by examiner

*Primary Examiner* — Susan McCormick Ewoldt
*Assistant Examiner* — Karen M Redden
(74) *Attorney, Agent, or Firm* — McKee, Voorhees & Sease, PLC

(57) ABSTRACT

A new cherry tree variety suitable for use as rootstock.

6 Drawing Sheets

Specification includes a Sequence Listing.

Botanical designation: The present invention relates to a new cherry tree variety. Based on a visual assessment of the seed parent, it appeared to be a species hybrid between two species within the *Prunus* subgenus CERASUS section Cerasus Koehne that are native to the collection region and cross naturally in the wild. These two species are *Prunus avium* L. and *Prunus fruticosa* Pall. The seed resulted from open-pollination and the paternal parent is unknown.

Variety denomination: The new plant has the varietal denomination 'Lake'.

BACKGROUND OF THE INVENTION

This invention relates to a new and distinct variety cherry tree. In the field of plant genetics, researchers conduct an extensive and continuing plant-breeding program including the organization and asexual reproduction of orchard trees, and of which plums, peaches, nectarines, apricots, cherries, almonds and interspecifics are exemplary. It was against this background of activities that the present variety of cherry tree was originated and asexually reproduced in our experimental orchard.

PRIOR VARIETIES

Among the existing varieties of cherry trees, which are known to us, and mentioned herein, 'Hedelfingen' (not patented); 'Montmorency' (not patented); and 'Bing' (not patented); 'GiSelA® 5' U.S. Plant Pat. No. 9,644 and 'GiSelA® 6' U.S. Plant Pat. No. 8,954.

ORIGIN OF THE VARIETY

Open-pollinated *Prunus* seeds were collected in hillsides surrounding Budapest, Hungary, and the seeds were then germinated at East Lansing, Mich. The plot of seedlings from which this variety was selected were sown in 1994 in a cultivated area in Clarksville, Mich. Selection of the present rootstock variety was initially based on observations of desirable traits to include its overall plant health, rooting capability and virus tolerance (Prune Dwarf Virus and *Prunus* Necrotic Ringspot Virus). The selected seedlings were then subjected to three trials for their use as a rootstock over the course of approximately fourteen years to select for desirable rootstock traits (Table 1). Selection of the present rootstock variety was then based upon observations that it induced excellent characteristics in the scion including reduced tree size measured as trunk cross-sectional area, reduced height, increased precocity, and high yields.

TABLE 1

| Trial | Activity | Year |
|---|---|---|
| 1 | Propagation of liners from softwood cuttings in commercial greenhouse in Grand Rapids, MI | 1 |

TABLE 1-continued

| Trial | Activity | Year |
|---|---|---|
| 1 | Liners sent and used to make test trees at Meadowlake Nursery in McMinnville, OR. Test trees were grafted with 'Hedefingen'and 'Bing' scions | 2-3 |
| 1 | Trees planted at test plot at Clarksville, MI (see discussion of Clarksville trial) | 4 |
| 2 | Propagation of liners from softwood cuttings at East Lansing, MI | 9 |
| 2 | Liners were sent to Willow Drive Nursery, Ephrata, WA to make test trees with 'Bing' scion | 10-11 |
| | Budwood from the mother block at Clarksville, MI was sent to the Clean Plant Network - Fruit Trees (Prosser, WA) and screened for virus resistance analysis[1] | 10 |
| 2 | The resulting trees were planted at the trial in Prosser, WA | 12 |
| 3 | Budwood of the MSU rootstocks was sent to Duarte Nursery, Hughson, CA to make liners for future trials | 9 |
| 3 | Duarte Nursery established meristem cultures and increased the liner number of the rootstocks using the meristem cultures | 9-11 |
| 3 | Rootstock liners were sent to Willow Drive Nursery, Euphrata, WA for budding with 'Montmorency' scions | 12-13[2] |
| 3 | Test trees were planted at a plot in Traverse City, MI with trials | 14 |

[1]Virus resistance analysis was not an independent trial, but occurred concurrently on or about year 10 of cultivation.
[2]Two years were required to make a budded tree As described above, selection of the present variety was based upon testing to evaluate the development of desirable traits, including overall plant health, virus tolerance (Prune Dwarf Virus and *Prunus* Necrotic Ringspot Virus), and rooting capabilities. In the first rootstock trial (Table 1), candidate rootstocks were grafted with 'Hedelfingen' and 'Bing' scions and planted in Clarksville, Mich. Further rootstock selection occurred on the basis of scion qualities to include precocity (early flowering and fruiting beginning the second year after planting) and reduced tree stature measured as trunk cross-sectional area. 'Lake' was asexually reproduced through conventional softwood cutting methods, and grafted with 'Bing' scion. For the second trial (Table 1), the 'Bing' trees grafted on the 'Lake' rootstock were planted in Prosser, Wash. and evaluated for scion trunk cross-sectional area, tree height, growth habit, flowers per node, crop yield, cropping efficiency, and fruit weight, among other traits. For the third rootstock trial (Table 1), 'Montmorency' trees grafted on the 'Lake' rootstock were planted in Traverse City, Mich. and evaluated for scion trunk cross-sectional area, yield, cropping efficiency and fruit weight among other traits. Cherry tree 'Lake' was selected from these trials.

ASEXUAL REPRODUCTION OF VARIETY

Asexual reproduction of the 'Lake' cherry rootstock has been achieved using the mother plant to obtain rooted liners using conventional softwood cutting procedures, and through meristem culture with commercial nurseries. Initially, liners were propagated from softwood cuttings in commercial greenhouses. A subset of these liners was used to establish a mother block in Clarksville, Mich. The remaining liners were sent to a nursery to make test trees of 'Lake' that were budded with the scions 'Hedefingen' and 'Bing'. The resulting trees were planted in a trial in Clarksville, Mich. A second set of liners was propagated from softwood cuttings in commercial greenhouses. These 'Lake' liners were budded with 'Bing' scion to make trees for a trial in Prosser, Wash. A nursery established meristem cultures of 'Lake', and using the plantlets produced they increased the liner number of 'Lake'. These liners were used to make trees with 'Montmorency' scion for a trial in Traverse City, Mich. The living tissues (i.e. leaves, stems, buds, flowers and fruits) of the original mother block plants were observed to be identical to secondary and tertiary vegetatively propagated plants.

STATEMENT OF STABILITY

Asexual propagation as described has demonstrated that the combination of traits that characterize this tree are fixed and remain true to type through at least two successive propagation cycles.

SUMMARY OF THE INVENTION

'Lake' is particularly useful as a rootstock. The variety results in dwarf trees with a significantly smaller canopy size than traditional non-dwarfing rootstocks and significantly smaller than trees on traditional rootstocks. When this variety is used as a rootstock for sweet cherry, the fruit can be harvested without using ladders. When used as a rootstock for sour cherry the fruit can be harvested by an over the row harvester that can move continuously down the row instead of being harvested by a trunk shaking machine that harvests each tree individually. The variety of the invention also has favorable precocity, which results in a scion variety having flower buds and fruit beginning in years two and three rather than years five or six when traditional rootstocks are used. 'Lake' was selected as a cherry rootstock on the basis of its scion's trunk cross-sectional area (TCSA), tree height, growth habit, flowers per node, crop yield, cropping efficiency, and fruit weight, among other traits, in two experimental field trials. Scion trees grafted onto this rootstock showed significant reduction in TCSA compared to other rootstocks. 'Lake' is suitable for standard nursery propagation practices for uniform liner production. 'Lake' can be distinguished from its parents and siblings by the use of Simple Sequence Repeat DNA markers. With primer pair PceGA59, 'Lake' is distinguished by the presence of the 189, 194 and 226 base pair (bp) alleles and the absence of the 182 and 186 bp alleles. With the primer pair PruG4RS, 'Lake' is distinguished by the strong presence of the 172 and 196 bp alleles, weak presence of the 190 allele, and the absence of 182, 192, 198 and 200 bp alleles.

BRIEF DESCRIPTION OF PHOTOGRAPHS

The accompanying photographs display flowers, leaves, and fruits from a self-rooted mother block tree at Clarksville, Mich.

DESCRIPTION OF THE NEW VARIETY

Figure 1:
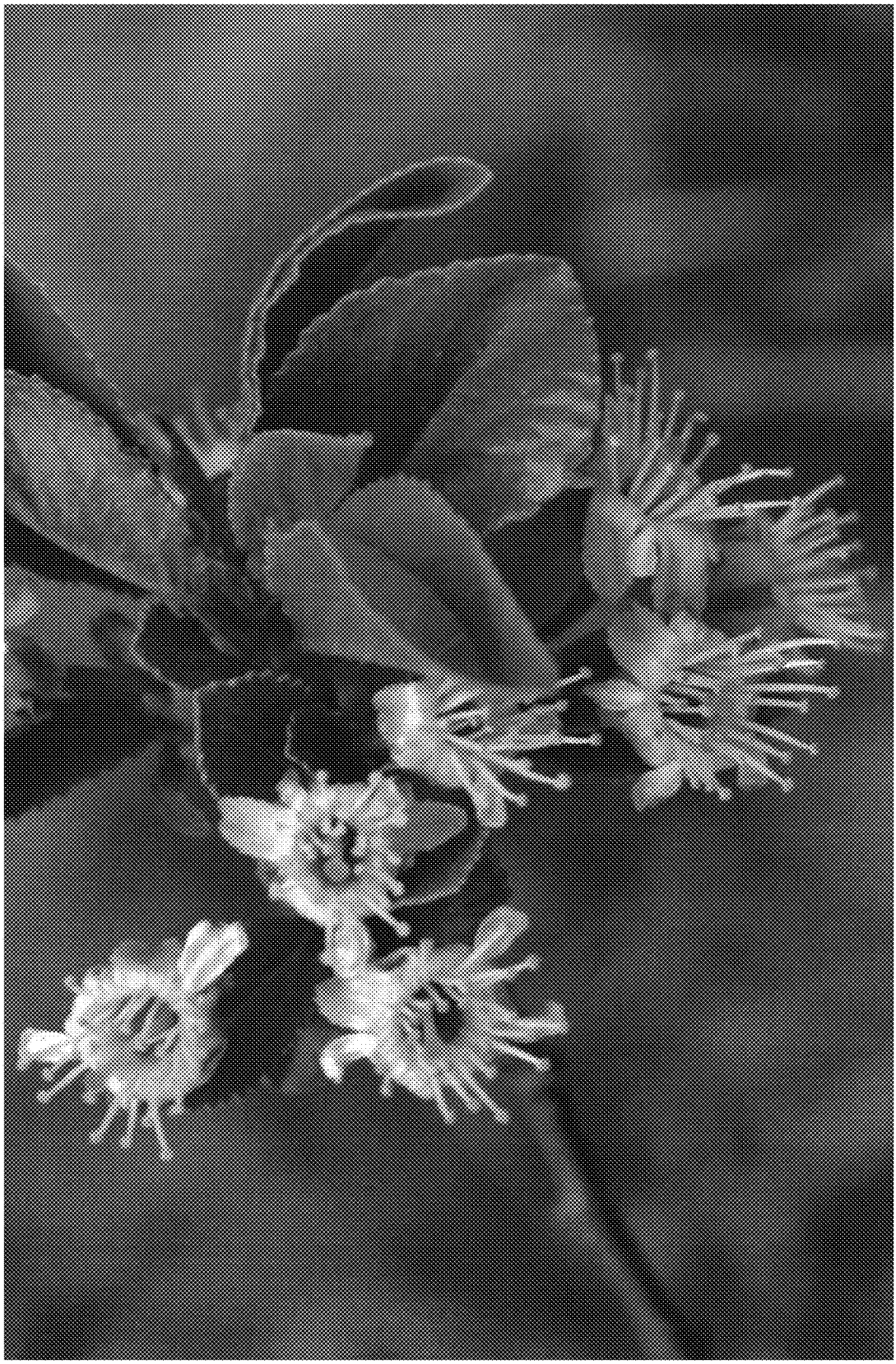
FIG. 1 is a photograph of the flowers of LAKE.
Figure 2:
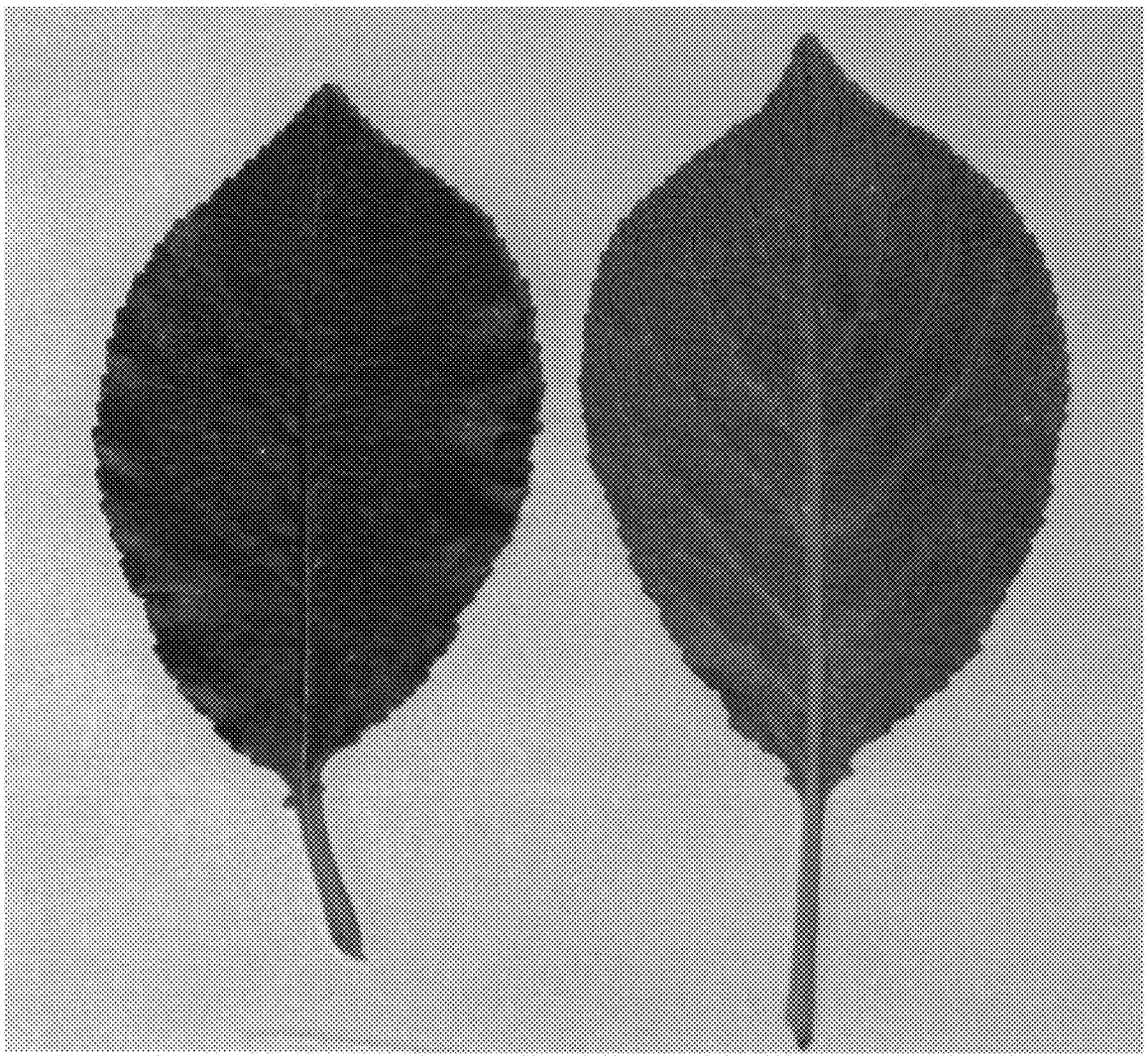
FIG. 2 is a photograph of two leaves of LAKE.
Figure 3:
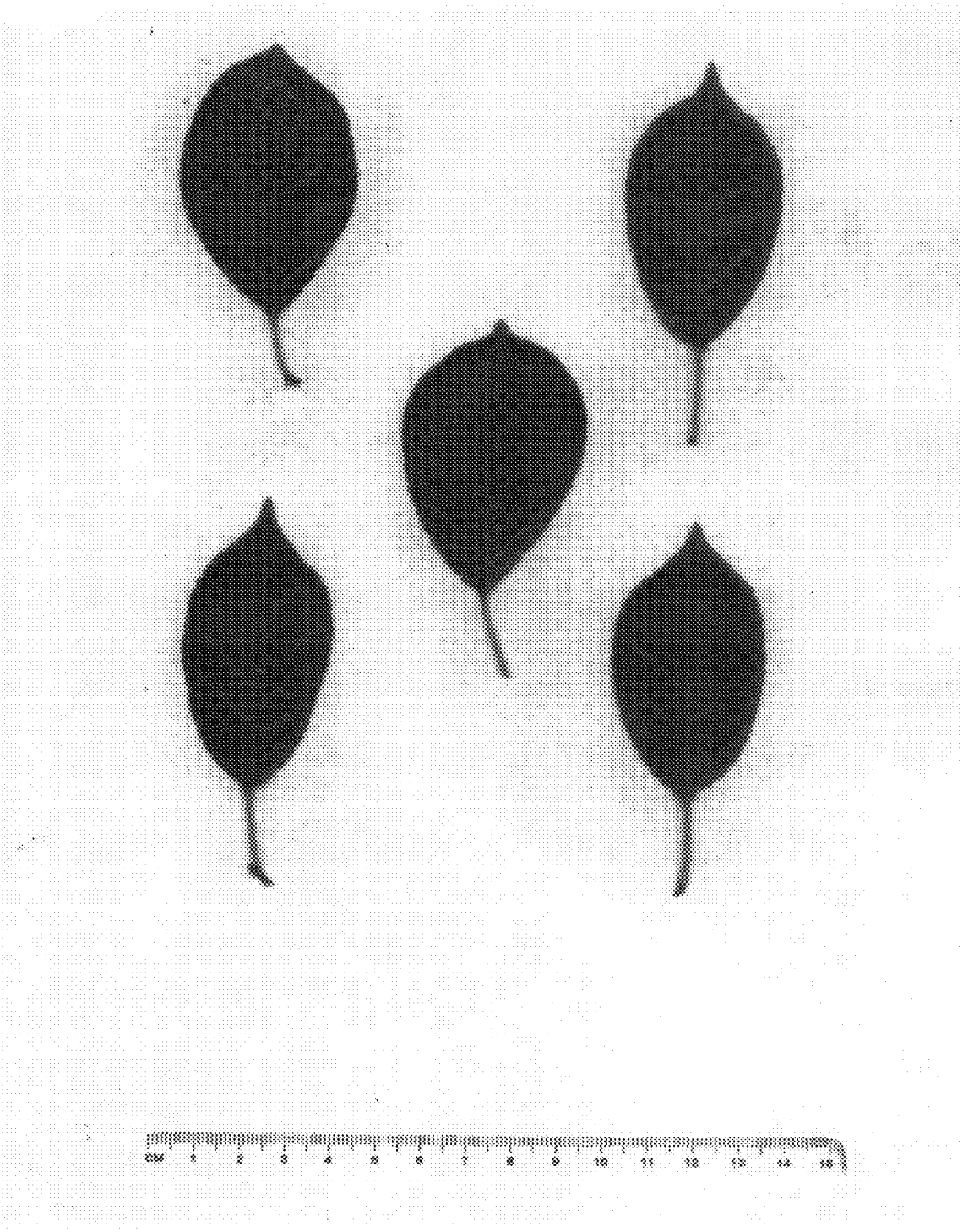
FIG. 3 is a photograph of five leaves of LAKE with a ruler to show size.
Figure 4:
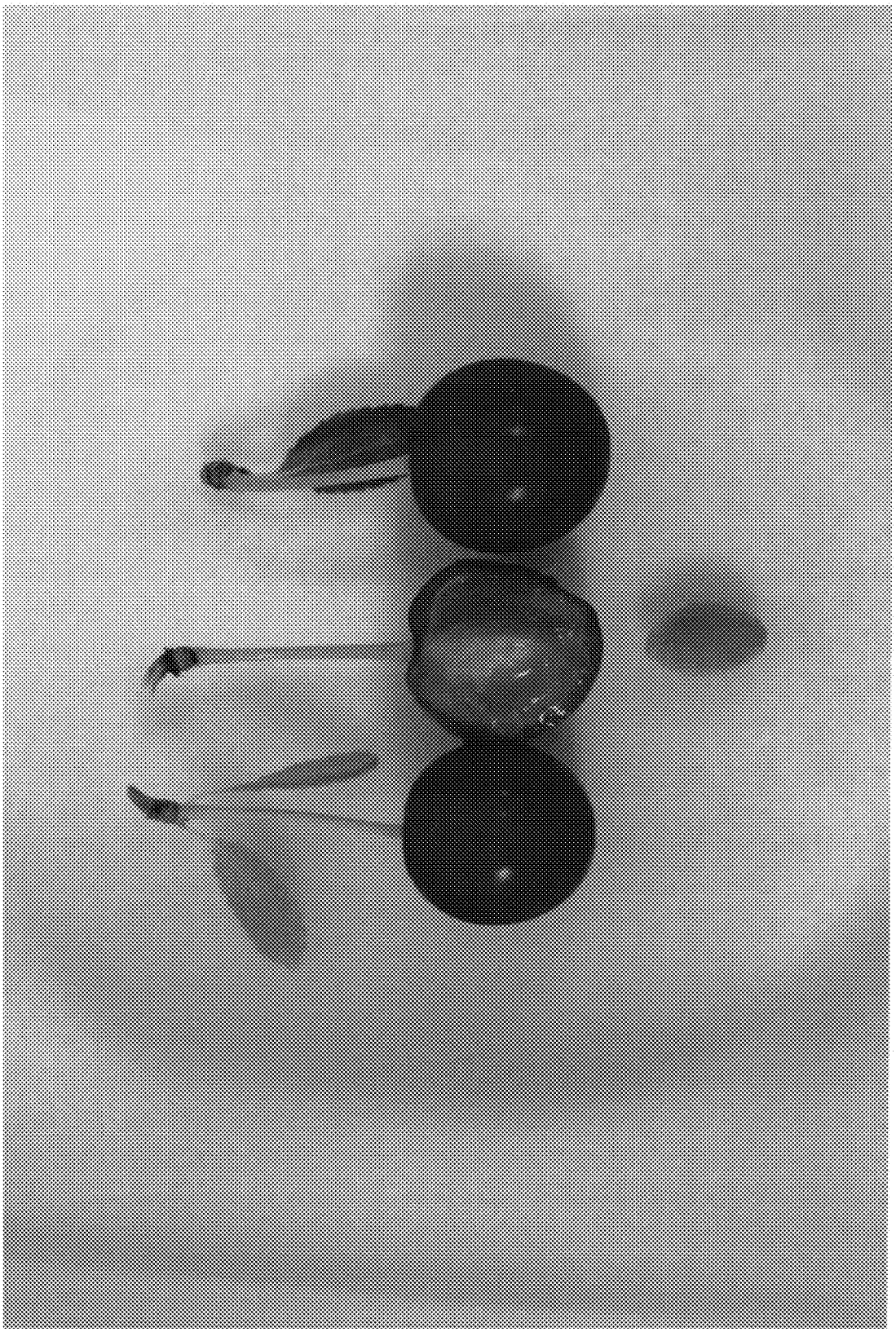
FIG. 4 is a photograph of cherries from and a seed from LAKE.
Figure 5:
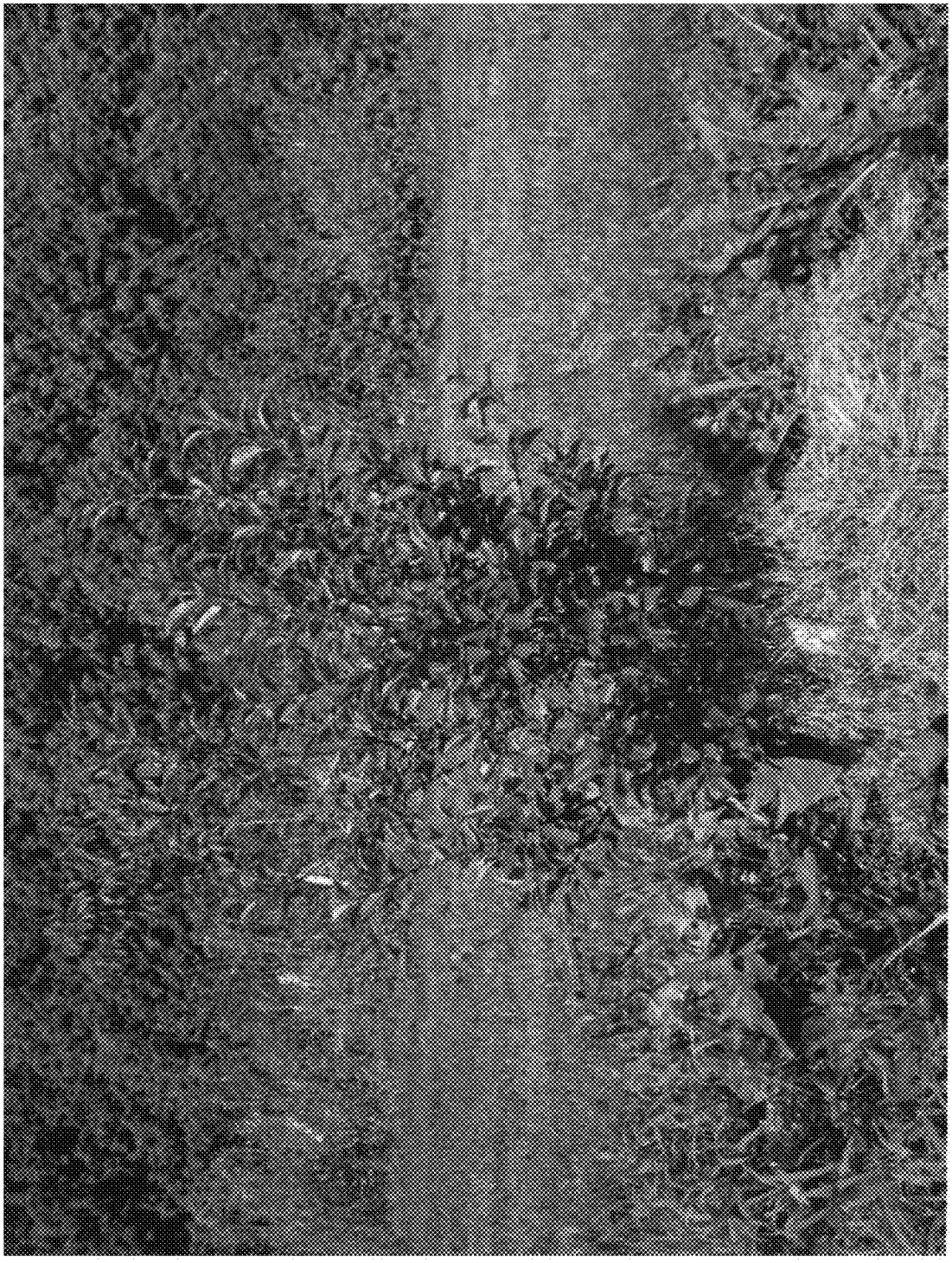
FIG. 5 is a photograph of the young tree of LAKE.
Figure 6:
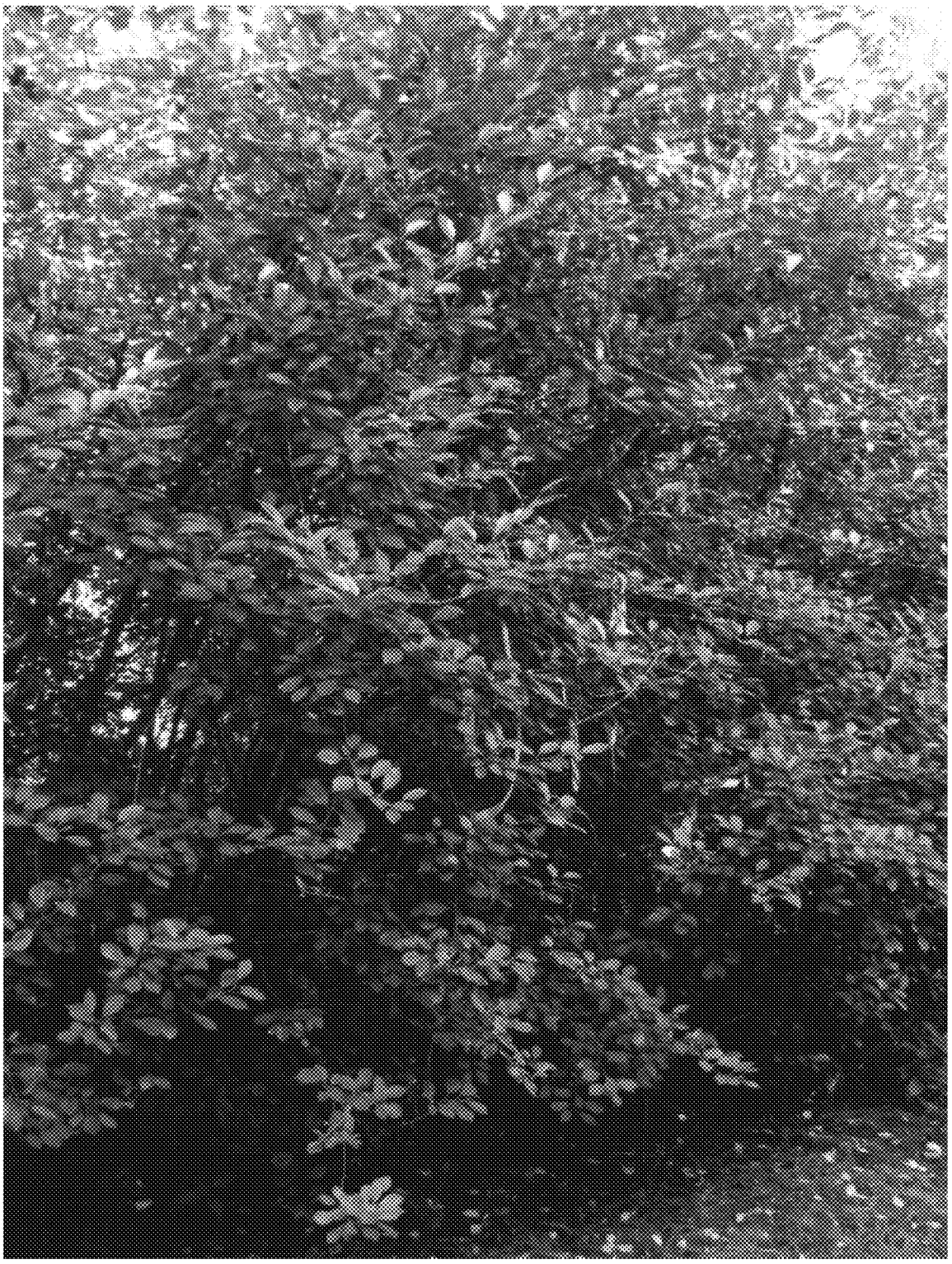
FIG. 6 is a photograph of an older tree of LAKE.

The following is a detailed botanical description of the new variety of cherry tree, its flowers, foliage and fruit, as based on observations of various aged specimens grown at Clarksville, Mich. with color in accordance with The Royal Horticultural Society Colour Chart (R.H.S.), 2001 edition.

Measurement Details

Flowers:

Inflorescence height: Measured from where the flower cluster attaches to the branch to the most distal floral part.

Flower diameter: Measured across the petals in mm.

Flower length: Measured from the bottom of the pedicel to the most distal flower point (mm).

Pedicel: The stem of an individual flower. It is measured from the attachment in the bud to the start of the perianth.

Peduncle: A stalk supporting an inflorescence. In these selections, the cherry flowers within a flower bud all start at the same base and then the stalk separates into individual pedicels supporting each flower.

Anther color: Before the anther's dehisce, when they are still bright yellow and plump.

Anther length: Measured for the longest anther measured from the top of the perianth tube.

Style: Measured above the swelled ovary.

Tree:

*Height*.—Approx. 10 ft.
*Diameter*.—Approx. 10 ft.
*Vigor*.—Weak.
*Branching habit*.—Spreading.
*Branching*.—Strong.
*Hardiness*.—Cold tolerant.
*Plant*.—Flowers: present.
*Scion compatibility confirmed*.—Hedelfingen, Bing, Montmorency.

Stem (trunk):

*Texture*.—Rough.
*Color*.—Grey brown 201A.

One year old shoot:

*Thickness*.—Thin.
*Length of internode* (*middle third of shoot—mean of* 10).—1.9 cm (1.5-2.5).
*Pubescence* (*upper third*).—Absent.
*Number of lenticels*.—6.
*Anthocyanin coloration of apex*.—Absent.
*Position of vegetative bud in relation to shoot*.—Slightly-markedly held out.
*Shape of apex of vegetative bud*.—Acute.
*Branching*.—Medium.

Leaves:

*Mature leaf arrangement*.—Alternate.
*Intensity of anthocyanin coloration of you leaf* (*during rapid growth*).—Weak.
*Leaf blade shape*.—Obovate.
*Leaf blade width*.—Narrow.
*Leaf blade*.—Ratio length to width: 1.9.
*Leaf length-blade only* (*cm*).—6.2.
*Leaf width* (*cm*).—3.5.
*Leaf blade angle of apex* (*excluding tip*).—Acute.
*Leaf blade shape of base*.—Obtuse.
*Leaf blade shape of apex* (*e.g., acute*).—Acute.
*Leaf blade; incisions of margin*.—Crenate.
*Leaf blade: depth of incisions of margin*.—Shallow.
*Leaf blade glossiness of upper side*.—Strong.
*Leaf blade: pubescence of lower side of apex*.—Weak.
*Leaf upper surface color* (*R.H.S.*).—137A.
*Leaf upper surface texture/pubescence*.—Smooth.
*Leaf upper surface venation color* (*R.H.S.*).—138A.
*Leaf venation pattern*.—Pinnate.
*Lower surface blade color* (*R.H.S.*).—137C.
*Leaf lower surface texture/pubescence*.—Weak pubescence.
*Leaf lower surface venation color* (*R.H.S.*).—138C.
*Leaf stipule frequency*.—Absent on expanded leaves.
*Petiole*.—Presence of pubescence of upper side: absent.
*Petiole*.—Intensity of pubescence of upper side: weak.
*Leaf petiole length* (*mm*).—16.
*Leaf petiole diameter* (*mm*).—1.2.
*Leaf petiole color* (*R.H.S.*).—138B.
*Leaf*.—Presence of nectaries: present.
*Varieties with nectaries only*.—Leaf — predominant number of nectaries: two.
*Leaf*.—Position of nectaries: base of leaf and petiole.
*Nectary color*.—Yellow.
*Nectary shape*.—Reniform.

Flowers:

*Flowers per cluster*.—2 to 4.
*Fragrance*.—None.
*Bloom date* (50%).—May 6, 2016.
*Inflorescence height* (*cm*).—2.8.
*Inflorescence diameter* (*cm*).—2.9.
*Flower diameter* (*mm*).—15.
*Flower length* (*mm*).—14.
*Petal number per flower*.—5.
*Petal arrangement*.—Flat whorl.
*Petal length* (*mm*).—7.5.
*Petal width* (*mm*).—4.5.
*Petal shape*.—Oval.
*Petal apex*.—Round.
*Petal margin*.—Smooth.
*Petal texture*.—Smooth.
*Petal when fully opened*.—Upper surface (R.H.S.): 155D.
*Petal when fully opened*.—Lower surface (R.H.S.): 155D.
*Sepal number*.—5 or 6.
*Sepal length* (*mm*).—5.
*Sepal width* (*mm*).—2.8.
*Sepal shape*.—Triangle.
*Sepal apex*.—Pointed.
*Sepal margin*.—Slightly serrated.
*Sepal texture*.—Smooth.
*Sepal color upper* (*R.H.S.*).—138B.
*Sepal color lower* (*R.H.S.*).—138B with some 59A.
*Flower pedicel length* (*mm*).—13.
*Flower pedicel diameter* (*mm*).—1.
*Flower pedicel angle* (*degrees*).—20.
*Flower pedicel texture*.—Smooth.
*Flower pedicel color* (*R.H.S.*).—138B.
*Flower peduncle length* (*mm*).—1.
*Flower peduncle diameter* (*mm*).—2.
*Flower peduncle texture*.—Smooth.
*Flower peduncle color*.—138B.
*Pistils; number per flower*.—1.
*Pistil length* (*mm*).—6 5.
*Pistil color* (*R.H.S.*).—149B.
*Style length* (*mm*).—7.
*Style color* (*R.H.S.*).—138C.
*Stigma shape*.—Round/indented.
*Stigma color* (*R.H.S.*).—138B.
*Stamens*.—Number per flower: 24 to 28.
*Longest filament length* (*mm*).—6.
*Filament color* (*R.H.S.*).—155D.
*Longest anther length* (*mm*).—7.
*Anther color* (*R.H.S.*).—20B.
*Pollen color* (*R.H.S.*).—17C.

*Pollen amount*.—Moderate.

Fruit:

*Mature fruit shape*.—Round.
*Mature fruit height* (*mm*).—17.9.
*Mature fruit width* 1 (*mm*).—16.3.
*Mature fruit width* 2 (*mm*).—18.1.
*Mature fruit ratio height/width* 2.—0.99.
*Mature fruit weight* (*g*).—3.8.
*Mature fruit flesh taste*.—Sour.
*Mature fruit skin color* (*R.H.S.*).—53A.
*Mature fruit flesh color* (*R.H.S.*).—23C.
*Stone color* (*R.H.S.*).—164D.
*Stone shape*.—Elongate.
*Stone number*.—1.
*Stone height* (*mm*).—11.8.
*Stone width* 1 (*mm*).—7.7.
*Stone width* 2 (*mm*).—6.2.
*Stone ratio height/width* 2.—1.91.
*Stone weight* (*g*).—0.31.
*Fruit stem length* (*mm*).—30.

Market use: Rootstock.

SIMPLE SEQUENCE REPEAT (SSR) MATERIALS AND METHODS

The use of clonally propagated *Prunus* sp. rootstocks in cherry production is increasing as these rootstocks provide reduced tree size and precocity. DNA markers that differentiate rootstocks are an important tool to verify identity among these rootstocks during the vegetative propagation stage. The simple sequence repeat (SSR) marker PceGA59 was previously determined to uniquely distinguish the commercially available GiSelA® rootstocks (Struss et al. 2002).

A targeted approach was used to develop a second SSR that was capable of providing differentiation of the rootstock selections of the invention and others by the inventors. The approach used was based on the ability to obtain genome-wide SNP (Single Nucleotide Polymorphism) data using the Illumina Infinium® cherry SNP array (Peace et al. 2012). An analysis of genome-wide SNP data for the rootstocks resulted in the identification of a genomic region on linkage group 4 that was likely to differ among the MSU rootstocks.

Using the peach genome sequence, an SSR marker was designed to target this region. This SSR marker, termed PruG4RS, successfully differentiated the MSU rootstocks. The development of PruG4RS and its combined use with PceGA59 has successfully circumvented the limitations of each individual marker and proven effective for use as a "quality control" DNA diagnostic tool for the commercial GiSelA® rootstocks as well as the MSU breeding program rootstock selections.

SSR Markers Used

Fingerprinting was performed using two simple sequence repeat (SSR) markers: PceGA59 and PruG4RS. The forward and reverse primers sequences for these two SSR markers are as follows:

TABLE 2

| Primer name | Primer sequence 5' → 3' |
|---|---|
| PceGA59_redesigned_F | TGAACCCCTCTACAAATTTTCC |
| PceGA59_redesigned_R | GACTGTAGAACCCAAAAGAACG |

TABLE 2-continued

| Primer name | Primer sequence 5' → 3' |
|---|---|
| PruG4RS - F | TCAGAAAAGAAATTGCAACGGG |
| PruG4RS - R | CTT AGT GGT CTA GTC TGC ATG C |

The first primer pair, PceGA59, was published in Struss et al. (2002). However, the primer sequence reflects the addition of GC clamps. Based on genetic data for the MSU cherry rootstocks we designed a second primer, PruG4RS (Andersen et al. 2015)

Plant Material Used and DNA Extraction

Cherry DNA was extracted from young unfolded leaf blades using the procedure of Edge-Garza et al. (2014).

Polymerase Chain Reaction (PCR)

PCR amplification was performed for the two SSRs using the following conditions: 94° C. for 5 min followed by 9 cycles of 94° C. for 30 s, 60° C. for 45 s (−1° C. per cycle), 72° C. for 1 min and then 24 cycles of 94° C. for 30 s, 55° C. for 45 s, 72° C. for 1 min with an elongation step of 72° C. for 5 min.

Gel Electrophoresis and Fragment Visualization

The PCR products were visualized by electrophoresis on a 6% denaturing polyacrylamide gel in a 50 cm Sequi-Gen GT vertical sequencing apparatus (Bio-Rad Laboratories, Hercules, Calif.) for 2.5 hours at 70 watts with 1× TBE buffer. Following electrophoresis, the gels were stained with the Silver Sequence DNA Sequencing System (Promega Corporation, Madison, Wis.) and dried for 24 hours. DNA fragment sizes were scored visually using 10 and 50 base pair ladders (Invitrogen Corporation, Carlsbad, Calif.).

TABLE 3

| DNA Fingerprint Data | | | | | | | | | | | | |
|---|---|---|---|---|---|---|---|---|---|---|---|---|
| | PceGA59 | | | | | | PruG4RS | | | | | |
| Allele (bp) | 182 | 186 | 189 | 194 | 226 | 172 | 182 | 190 | 192 | 196 | 198 | 200 |
| 'Lake' | | | + | + | + | + | | + | | + | | |
| Gi5 | + | + | | + | | | | | + | | | + |
| Gi6 | + | | + | | + | | | | + | | | + |

The following references for determination of various alleles, are hereby incorporated in their entirety.

Struss D, Boritzki M, Karle R, and Iezzoni A F. 2002. Microsatellite markers differentiate eight Giessen cherry rootstocks. Hort Science 37: 191-193.

Andersen K, Sebolt A, Stegmeir T, Iezzoni A. 2015. Development of the Simple Sequence Repeat marker PruG4RS for the differentiation of cherry rootstocks. American Society for Horticultural Sciences Annual Conference, New Orleans, La., August 4-7, Poster #023.

Edge-Garza, D., Rowland, T., Haendiges, S. and Peace, C. 2014. A high-throughput and cost-efficient DNA extraction protocol for the tree fruit crops apple, sweet cherry, and peach relying on silica beads during tissue sampling. Molecular Breeding 34:2225-2228.

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1 tgaacccctc tacaaatttt cc 22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2 gactgtagaa cccaaaagaa cg 22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3 tcagaaaaga aattgcaacg gg 22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4 cttagtggtc tagtctgcat gc 22

I claim:

1. A new and distinct variety of cherry tree substantially as described and illustrated herein.

* * * * *